United States Patent
Gallagher (10) Patent No.: US 11,002,644 B2
(45) Date of Patent: May 11, 2021

(54) HYBRID PRODUCT SAMPLING SYSTEM EMPLOYING SUCTION AND DISCHARGE LINES

(71) Applicant: Savant Measurement Corporation, Kingwood, TX (US)

(72) Inventor: James E. Gallagher, Kingwood, TX (US)

(73) Assignee: Savant Measurement Corporation, Kingwood, TX (US)

(*) Notice: Subject to any disclaimer, the term of this patent is extended or adjusted under 35 U.S.C. 154(b) by 177 days.

(21) Appl. No.: 16/297,675

(22) Filed: Mar. 10, 2019

(65) Prior Publication Data
US 2019/0204187 A1    Jul. 4, 2019

Related U.S. Application Data (62) Division of application No. 15/381,522, filed on Dec. 16, 2016, now Pat. No. 10,228,309.

(Continued)

(51) Int. Cl.
| | | |
|---|---|---|
| *G01N 1/10* | (2006.01) | |
| *G01N 1/14* | (2006.01) | |
| *G01N 33/28* | (2006.01) | |
| *G01N 1/38* | (2006.01) | |

(52) U.S. Cl.
CPC ............ *G01N 1/10* (2013.01); *G01N 1/14* (2013.01); *G01N 33/2835* (2013.01); *G01N 1/38* (2013.01);

(Continued)

(58) Field of Classification Search
CPC .... G01N 1/10; G01N 2001/1031; G01N 1/14; G01N 1/18; G01N 1/22; G01N 1/2247;
(Continued)

(56) References Cited

U.S. PATENT DOCUMENTS

| 3,403,544 A | 10/1968 | Francisco, Jr. |
| 3,720,092 A | 3/1973 | Reinecke |

(Continued)

FOREIGN PATENT DOCUMENTS

| JP | 2008125896 | 9/2008 |
| JP | 5944625 | 11/2011 |

OTHER PUBLICATIONS

Honeywell International Inc. ©, Process Solutions-"Pipe Provers vs. Small Volume Provers: Long-Term Thinking for Better Custody Transfer Solutions", dated Mar. 2015, (10 pages).

*Primary Examiner* — Robert R Raevis
(74) *Attorney, Agent, or Firm* — Clark Hill Strasburger (57) ABSTRACT

A system and method for sampling of liquid products. The system includes a portable, releaseably connected product sample receiving assembly and a plurality of product sampling and mixing assemblies. The product sample receiving assembly can be attached and detached from two or more the product sampling and mixing assemblies, so that a single product sample receiving assembly can be used to service multiple product sampling and mixing assembly locations at different times. Each of the multiple product sampling and mixing assemblies includes a suction assembly and a discharge assembly on opposite sides of a static mixer. The product sample receiving assembly may include a slipstream configuration or in-line configuration. The product sampling and mixing assemblies may be unidirectional or bidirectional.

8 Claims, 8 Drawing Sheets

Related U.S. Application Data (60) Provisional application No. 62/269,151, filed on Dec. 18, 2015, provisional application No. 62/269,219, filed on Dec. 18, 2015.

(52) U.S. Cl.
CPC .............. *G01N 2001/1031* (2013.01); *G01N 2001/1093* (2013.01)

(58) Field of Classification Search
CPC ............ G01N 1/26; G01N 2001/1087; G01N 2001/1093; G01N 1/38
USPC .............. 73/863.01–863.03, 863.31, 863.33, 73/863.41, 863.43–863.45, 863.56, 73/863.81–863.86; 366/140
See application file for complete search history.

(56) References Cited

U.S. PATENT DOCUMENTS

| | | |
|---|---|---|
| 3,978,708 A | 9/1976 | Hayward |
| 4,128,002 A | 12/1978 | Cameron |
| 4,347,731 A | 9/1982 | Fisher |
| 4,606,218 A | 8/1986 | Chisman, III |
| 4,628,724 A | 12/1986 | Maurer |
| 4,829,808 A | 5/1989 | West |
| 5,392,632 A | 2/1995 | Umeda |
| 5,440,925 A | 8/1995 | Padden |
| 7,220,383 B2 | 5/2007 | Anderson |
| 7,650,775 B2 | 1/2010 | Ignatian |
| 7,716,963 B2 | 5/2010 | Bell |
| 8,161,791 B2 | 4/2012 | Ignatian |
| 8,505,355 B2 | 8/2013 | Rudroff |
| 8,511,138 B2 | 8/2013 | Larsen |
| 8,826,717 B2 | 9/2014 | Van Bekkum |
| 8,950,235 B2 | 2/2015 | Heath |
| 9,021,855 B2 | 5/2015 | Delatorre |
| 9,103,709 B2 | 8/2015 | Brown |
| 10,228,309 B2 * | 3/2019 | Gallagher ............... G01N 1/10 |
| 2007/0068241 A1 | 3/2007 | Bains |
| 2007/0119227 A1 | 5/2007 | Moriyama |
| 2008/0250848 A1 | 10/2008 | Karki |
| 2014/0137625 A1 | 5/2014 | Murnane, Jr. |
| 2015/0308882 A1 | 10/2015 | Yoshimoto |

\* cited by examiner

HYBRID PRODUCT SAMPLING SYSTEM EMPLOYING SUCTION AND DISCHARGE LINES

BACKGROUND OF THE DISCLOSURE

1. Field of the Disclosure

This disclosure relates to the field of material sampling and analysis and, more specifically, to methods and devices for sampling fluid products, such as crude oil.

2. Description of the Related Art

Sampling of fluid products is performed so that the representative properties and compositions of the fluid products can be estimated based on analysis of a small subset of the whole (e.g. an accurate sample). In order for sampling to be effective in estimating the composition of a larger quantity of fluid, the sample that is extracted must be truly representative of the larger quantity.

When a fluid is evenly mixed, the sample is most likely representative of the fluid as a whole, thus, the fluid may be mixed prior to the sampling taking place. This even mixing provides that all of the fluid is moving at the same linear velocity past a flow stream into which a sampling probe is inserted. Sampling while the components of a mixture are at the same linear velocity is called isokinetic sampling. While the fluid is thoroughly mixed, the sample is extracted from the fluid stream and set aside for analysis.

Isokinetic product sampling systems involve permanent installations with significant associated costs. Often located near transportation or loading hubs where custody transfer can take place, product sampling systems for transport of crude oil may cost $1,500,000 or more.

A shortcoming of prior art product sampling systems is the high cost of installation and installed equipment. Another shortcoming, related to the high cost, is that sampling systems may not be cost effective for the amount of product to be transported, leading to parties or transporters to install product sampling systems at a loss or to forgo installation of a traditional product sampling system in favor of a lower cost and lower accuracy solution. Another shortcoming of prior art product sampling systems is that, due to their size, they can only be used at a single location without extensive cost and time for disassembly and reassembly. Another shortcoming is that sampling systems are unidirectional.

For these reasons there is a need to develop a product sampling system that is more cost effective than traditional product sampling systems.

BRIEF SUMMARY OF THE DISCLOSURE

In aspects, the present disclosure is related to methods and apparatuses for fluid sampling, specifically for liquid products.

One embodiment according to the present disclosure includes a product sampling system including: a product sample receiving assembly suitable for liquid fluids; a first product sampling and mixing assembly releaseably connected to the product sample receiving assembly; a second product sampling and mixing assembly, wherein the product sample receiving assembly is configured to connect with the second product sampling and mixing assembly when the product sample receiving assembly is detached from the first product sampling and mixing assembly. The first and second product sampling and mixing assemblies may each include: a tubular; a static mixer disposed in the tubular, wherein the static mixer defines an upstream side and a downstream side of the tubular; a sampler probe disposed on the downstream side of the tubular; a water injection port disposed on the upstream side of the tubular; and a flow meter disposed on the upstream side of the tubular between the water injection port and the static mixer. One or both of the first and second product sampling and mixing assemblies may further include: a spot sample port on the downstream side of the tubular. The product sample receiving assembly may include a flow meter in fluid communication with the sampler probe; and a transportation container in fluid communication with the flow meter.

Another embodiment according to the present disclosure is a method of operating a product sampling system comprising: obtain a sample of product from a first product sampling and mixing assembly with a product sample receiving assembly; detach the product sample receiving assembly from the first product sampling and mixing assembly; and attach the product sample receiving assembly to a second product sampling and mixing assembly, wherein both of the first and second product sampling and mixing assemblies are configured to be releaseably attached to the product sample receiving assembly.

Examples of the more important features of the disclosure have been summarized rather broadly in order that the detailed description thereof that follows may be better understood and in order that the contributions they represent to the art may be appreciated. There are, of course, additional features of the disclosure that will be described hereinafter and which will form the subject of the claims appended hereto.

BRIEF DESCRIPTION OF THE DRAWINGS

A better understanding of the present disclosure can be obtained with the following detailed descriptions of the various disclosed embodiments in the drawings, which are given by way of illustration only, and thus are not limiting the present disclosure, and wherein.

While the inventions disclosed herein are susceptible to various modifications and alternative forms, only a few specific embodiments are shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art, and to enable such persons to make and use one or more of the inventive concepts.

DETAILED DESCRIPTION OF THE DISCLOSURE

In aspects, the present disclosure is related to methods and apparatuses for fluid sampling. Specifically, the present disclosure is related to measurement of a flowing liquid product, such as crude oil. The present invention is susceptible to embodiments of different forms. There are shown in the drawings, and herein will be described in detail, specific embodiments with the understanding that the present invention is to be considered an exemplification of the principles and is not intended to limit the present invention to that illustrated and described herein.

One or more illustrative embodiments incorporating the invention disclosed herein are presented below. Not all features of an actual implementation are described or shown in this application for the sake of clarity. It is understood that in the development of an actual embodiment incorporating the present invention, numerous implementation-specific decisions must be made to achieve the developer's goals, such as compliance with system-related, business-related, government-related and other constraints, which vary by implementation from time to time. While a developer's efforts might be complex and time consuming, such efforts would be, nevertheless, a routine undertaking for those of ordinary skill in the art having the benefit of this disclosure.

Accordingly, it is an object of the present invention to provide a hybrid product sampling system and apparatus, as well as an associated method, to enable an operator to reduce cost multiple product sampling system installations. It is also an object of the invention to provide a sampling assembly that can be used with multiple mixing assemblies.

While apparatuses and methods are described in terms of "comprising" various components or steps (interpreted as meaning "including, but not limited to"), the compositions and methods can also "consist essentially of" or "consist of" the various components and steps, such terminology should be interpreted as defining essentially closed-member groups.

Figure 1:
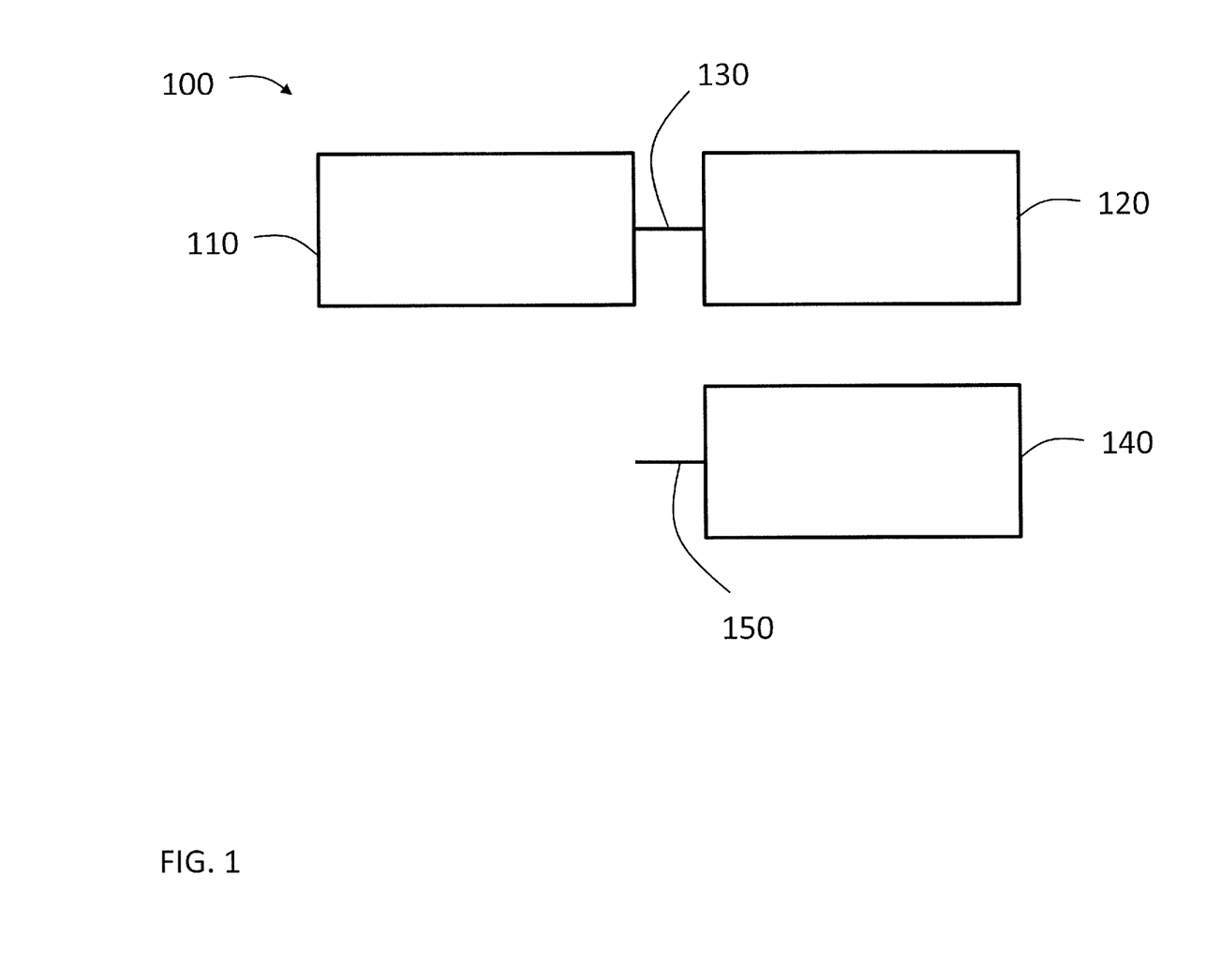
FIG. 1 shows a diagram of a product sampling system according to one embodiment of the present disclosure.

FIG. 1 shows a product sampling system 100, which includes a product sample receiving assembly 110 and a product sampling and mixing assembly 120. The product may be transferred from the product sampling and mixing assembly 120 to the product sample receiving assembly 110 through a tubular 130. The tubular 130 may be part of the product sampling system 110 or part of the product sampling and mixing assembly 120. As shown in FIG. 1, the tubular 130 is part of the product sampling and mixing assembly 120. The product sampling system 100 may also include one or more additional product sampling and mixing assemblies 140. In some embodiments, each of the one or more additional product sampling and mixing assemblies 140 may have an associated tubular 150.

The associated tubular 150 may be optional, especially if the tubular 130 is associated with the product sample receiving assembly 110. In some embodiments, tubular 130 and/or tubular 150 may be optional. The product receiving assembly 110 and the first and second product sampling and mixing assemblies 120, 140 may be directly connected to one another. Regardless of a direct connection or connection through a tubular 130, 150, the product receiving assembly 110 can be releaseably connected to the first and second product sampling and mixing assemblies 120, 140. The releaseable connection between the product receiving assembly 110 and the first and second product sampling and mixing assemblies 120, 140 may be made by connector known to persons of ordinary skill in the art to be suitable for fluid sampling and custody transfer systems, and in particular, liquid fluid sampling and custody transfer systems.

Figure 2A:
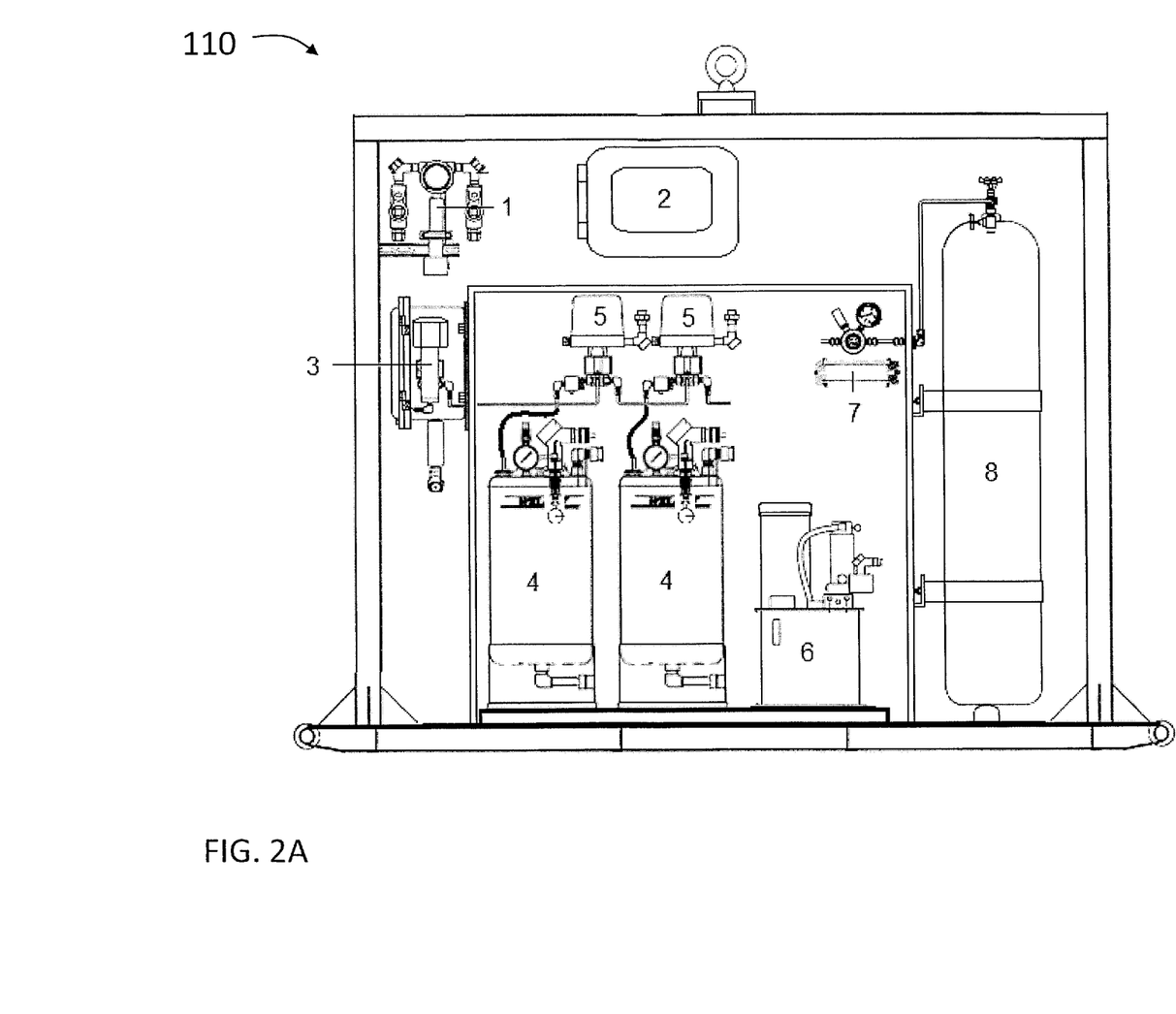
FIG. 2A shows a diagram of an embodiment of a detachable sampling assembly in accordance with FIG. 1.

FIG. 2A shows an embodiment of the product sample receiving assembly 110 for use with FIG. 1. The product sample receiving assembly 110 may include a flow meter 1, a programmable logic controller (PLC) 2, a flow switch 3, one or more transportation containers 4, a selector valve 5, a hydraulic unit with solenoid 6, a volume cylinder with regulator 7, and a purge gas tank 8. The flow meter 1 is configured to measure the flow of the product to be sampled into the product sample receiving assembly 110. Products that may be sampled by the product sample receiving assembly 110 may include, but are not limited to, crude oil, hydrocarbon liquids, refined liquids, condensate, and water. The PLC controller 2 is configured to receive information for identifying the sample, including batch size, as well as, to control operation of the product sample receiving assembly 110 and to print out information regarding the sample. The flow switch 3 or "bite checker" detects whether a sample probe 9 (see FIG. 2B) on the product sampling and mixing assembly 120 has been injected into one of the transportation containers 4. The flow switch 3 may be a time delayed flow switch. The flow switch 3 is optional. The one or more transportation containers 4 are configured to receive the product sample and be detached from the product sample receiving assembly 110 for transport. Suitable transportation containers include portable sampling containers. The selector valve 5 is optional and used to select the transportation container 4 to receive the product sample when two or more transportation containers 4 are present. The hydraulic unit with solenoid 6 is optional. The hydraulic unit 6 is configured to operate a sampler in the product sampling and mixing assembly 120 when receiving a control signal from the PLC controller 2. The volume cylinder with regulator 7 is configured to purge the product sampler with gas that is non-reactive with the product and the sample receiving equipment, such as nitrogen. The purge gas tank 8 holds the non-reactive gas that is used to purge the product sampler. In some embodiments, the volume cylinder with regulator 7 and the purge gas tank 8 may be optional. The product sample receiving assembly 110 may also include an electrical power supply (AC/DC) (not shown).

Figure 2B:
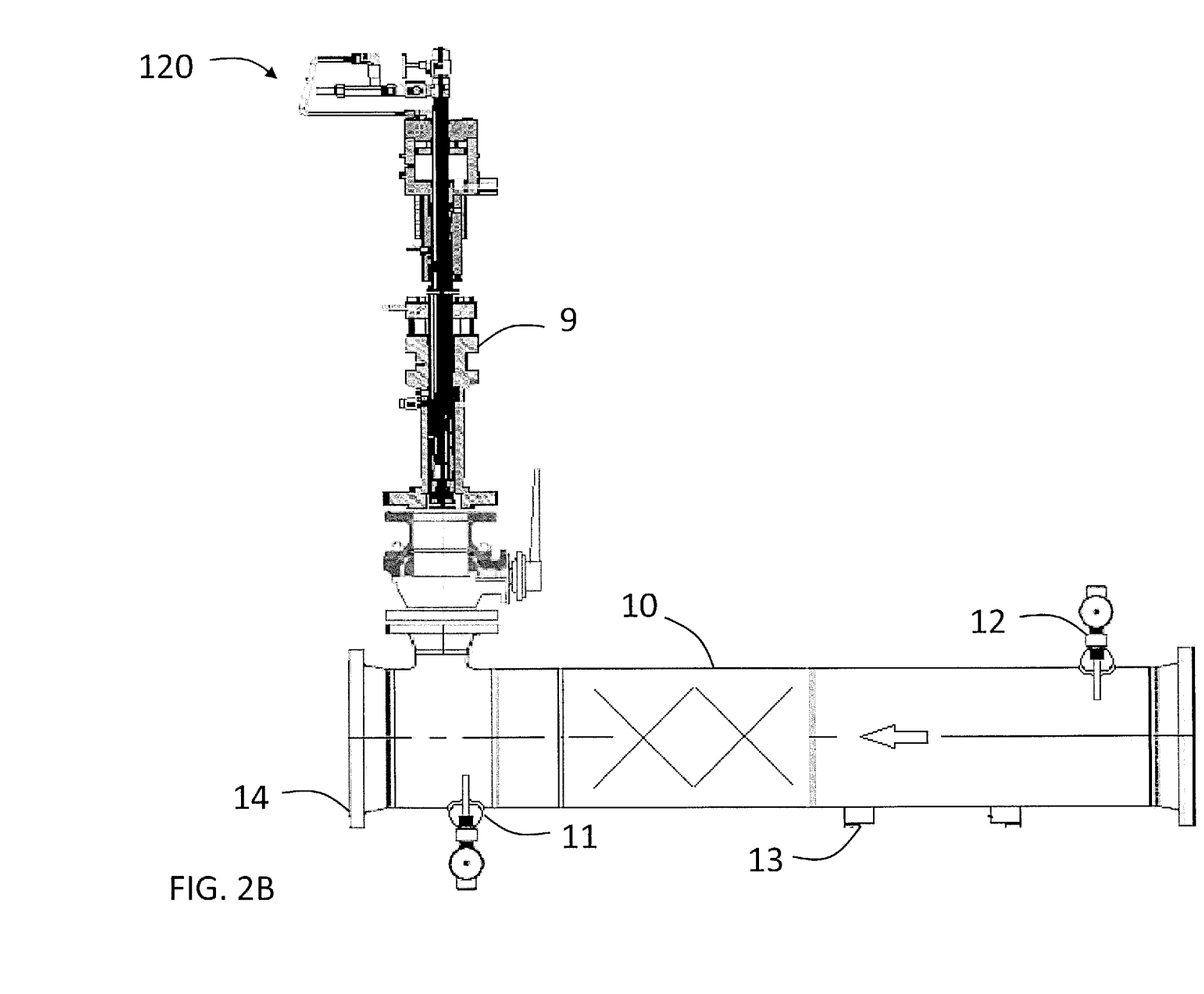
FIG. 2B shows a diagram of an embodiment of a permanent mixing assembly and sample port in accordance with FIG. 1.

FIG. 2B shows an embodiment of the product sampling and mixing assembly 120 in accordance with FIG. 1. The product sampling and mixing assembly 120 includes the sample probe 9, a static mixer 10, a spot sample port 11, a water injection port 12, one or more flow meters 13, and a tubular 14. The sample probe 9 is disposed in the tubular 14 on the output side of the static mixer 10, which is disposed within the tubular 14. The tubular 14 is substantially straight, and the static mixer 10 defines the upstream and downstream portions of the tubular 14. The sample probe 9 is configured to draw a sample of fluid out of the flow stream of the fluid in the tubular 14 and exiting the static mixer 10. In some embodiments, the sampler probe 9 may be an automatic sampler probe. The static mixer 10 mixes the liquid fluid to be sampled with free water. The spot sample port 11 is disposed in the tubular 14 in proximity to the sample probe 9 and downstream of the static mixer 10. In some embodiments, the sample probe 9 may be upstream of the static mixer 10. The water injection port 12 is shown disposed in the tubular 14 upstream of the static mixer 10; however, the water injection port 12 may be disposed upstream or downstream of the static mixer 10. Between the static mixer 10 and the water injection port 12, at least one flow meter 13 is disposed in or on the tubular 14. The position of the flow meter 13 is exemplary and illustrative only, as the flow meter 13 may be disposed in other locations along the tubular 14 as would be understood by a person of skill in the art. The at least one flow meter 13 may be any flow measurement device suitable as understood by a person of ordinary skill in the art. Non-limiting exemplary flow meters 13 may include an insertion flow meter and an ultrasonic liquid flowmeter.

Figure 3:
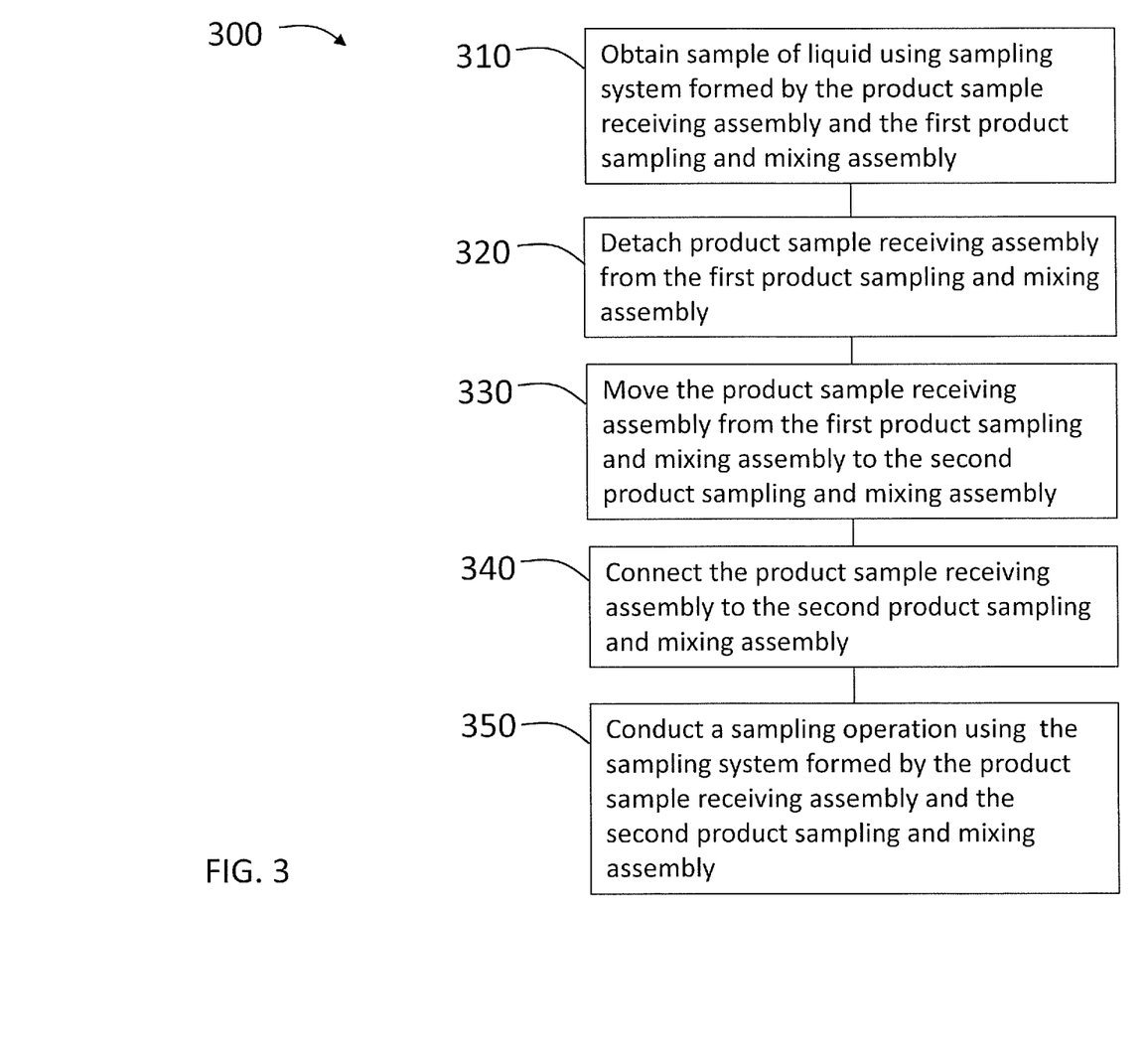
FIG. 3 shows a flow chart of an embodiment of a method for using the detachable product sample receiving assembly with multiple product sampling and mixing assemblies in accordance with FIG. 1.

FIG. 3 shows a flow chart of one embodiment of a method 300 for operating product sampling system 100. In step 310, the product sample receiving assembly 110 is in communication with the product sampling and mixing assembly 120. A sample of the product may be obtained with the product sampling and mixing assembly 120 and transferred to the sample receiving assembly 110 in a manner understood by a person of ordinary skill in the art. In step 320, the product sample receiving assembly 110 is detached from the product sampling and mixing assembly 120. In step 330 the product sample receiving assembly 110 is move to the additional product sampling and mixing assembly 140. In step 340, the product sample receiving assembly 110 is connected with the additional product sampling and mixing assembly 140. In step 350, fluid is introduced to the static mixer in the product sampling and mixing assembly 140 and the sample is taken. These steps can be repeated for as many additional product sampling and mixing assemblies 140 are available. Through this method, the detachable product sample receiving assembly 110 provides a moveable, low cost alternative to a complete installation where the entire sampling and mixing operation are performed by a single unit. The reusability of the detachable product sample receiving assembly 110 allows a single product sample receiving assembly 110 to be reused at multiple product sampling and mixing assemblies 140 at various locations.

Figure 4A:
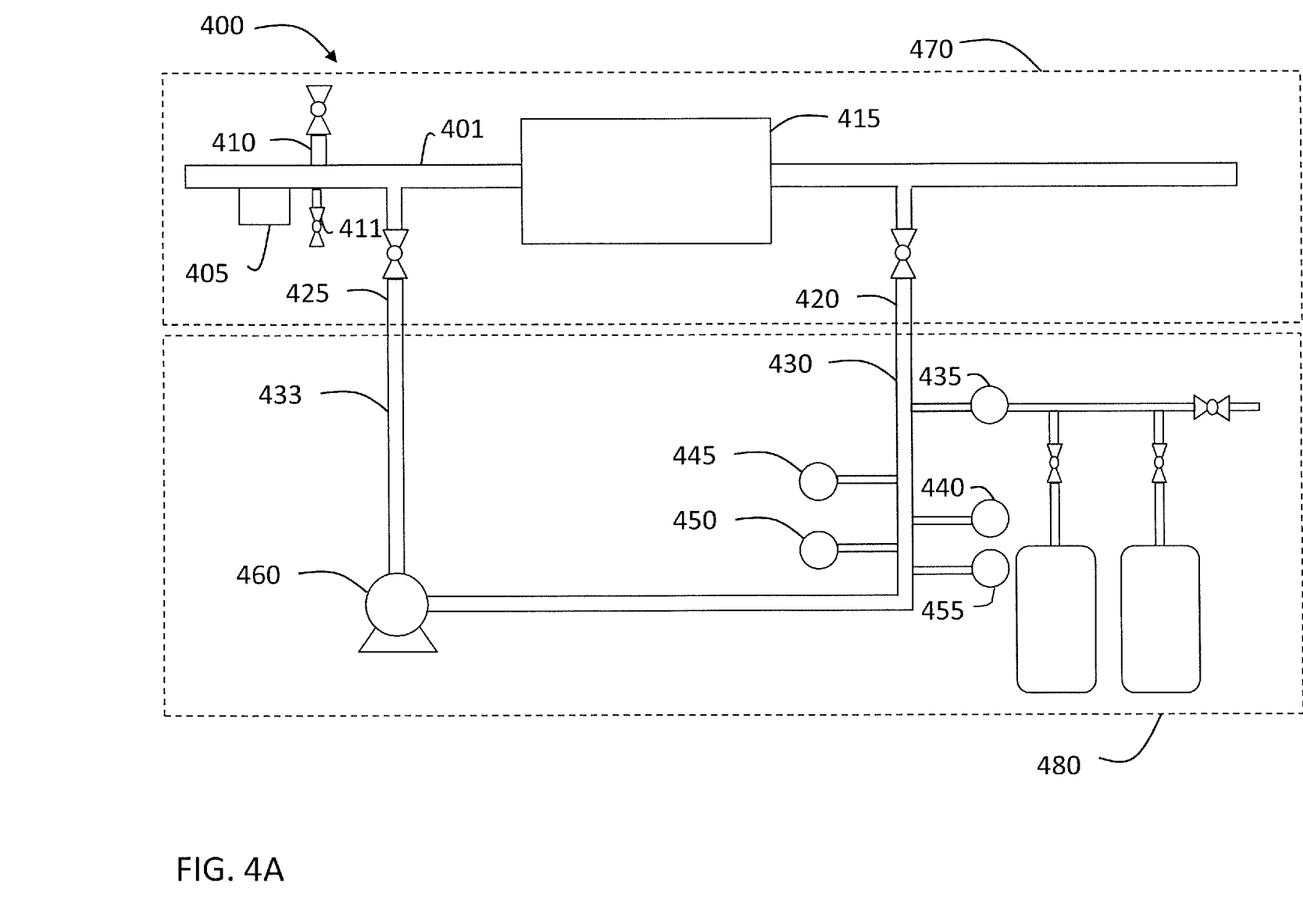
FIG. 4A shows a diagram of an embodiment of a product sampling and mixing assembly and portable sampling assembly with a slip-stream configuration in accordance with FIG. 1.
Figure 5:
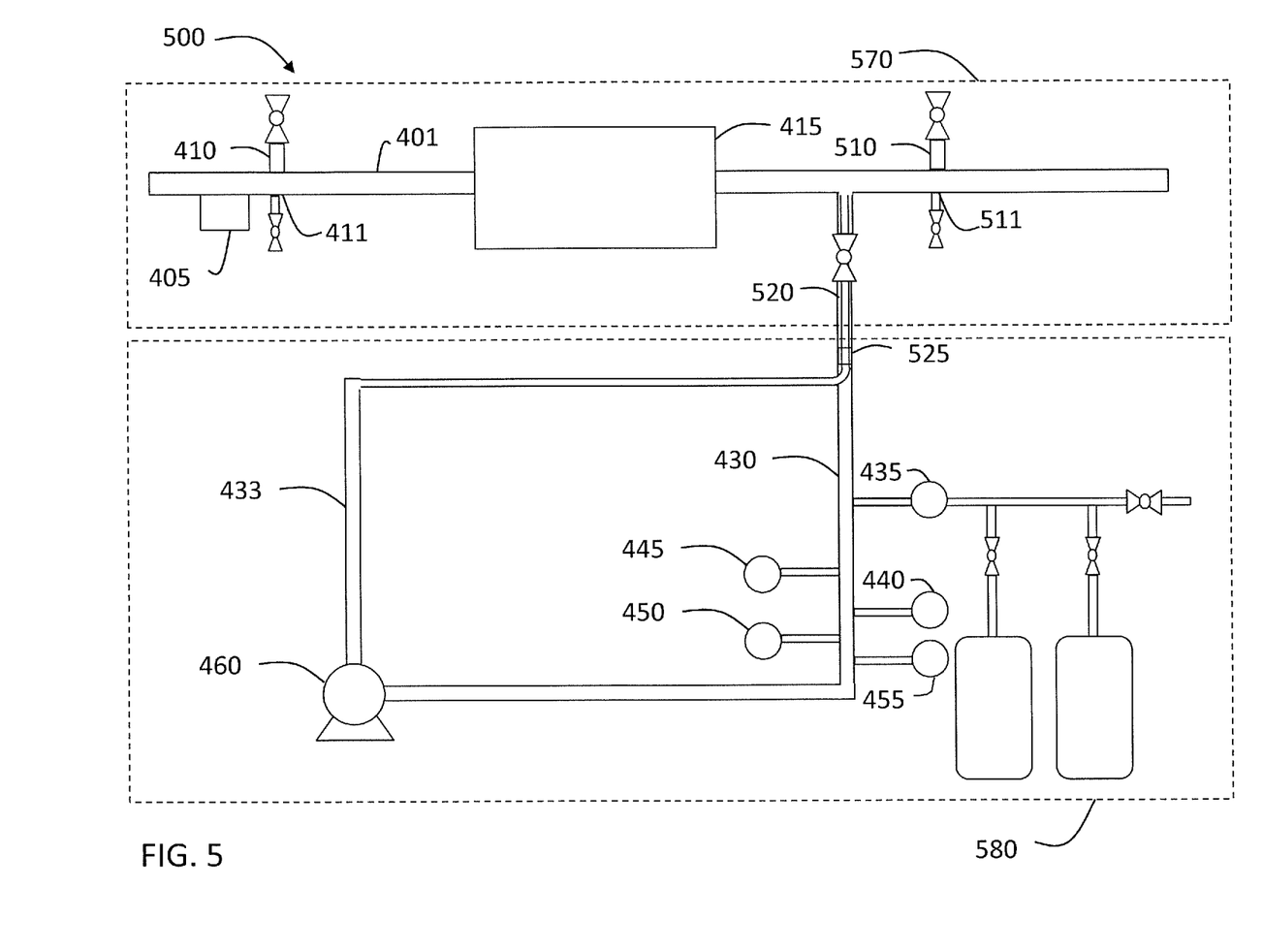
FIG. 5 shows a diagram of another embodiment of a bidirectional product sampling and mixing assembly and portable sampling assembly with a slip-stream configuration in accordance with FIG. 1.

FIG. 4A shows a slip-stream hybrid product sampling system 400, which includes a product sampling and mixing assembly 470 and a sample receiving assembly 480. The product sampling and mixing assembly 470 is comparable to the product sampling and mixing assembly 120, and the sample receiving assembly 480 is comparable to the sample receiving assembly 110, thus both may be configured as shown in FIG. 1 and use the method 300 as shown in FIG. 3. An additional product sampling and mixing assembly 470 may be used as the additional product sampling and mixing assembly 140. The product sampling and mixing assembly 470 includes a flow line 401 that carries the product to be sampled. A flowmeter 405 is coupled to the flow line 401 to measure the rate of flow of the product. The flowmeter 405 may include an insertion flowmeter, an ultrasonic flowmeter, or another suitable flowmeter as would be understood by one of ordinary skill in the art. A water injection line 410 is coupled to the flow line 401 to allow water to be injected into the product flow. The water injection line 410 is disposed downstream of the flowmeter 405. The position of the water injection line 410 is illustrative and exemplary only, as the water injection line 410 may be disposed upstream of the flowmeter 405 as well. A spot sample port 411 may be coupled to and receive fluid from the flow line 401. A static mixer 415 is disposed in-line with the flow line 401 to mix the product with the injected water. A suction assembly 420 is disposed on the flow line 401 downstream of the static mixer 415. The suction assembly 420 includes piping and a valve to control product flow between the flow line 401 and the sample receiving assembly 480. A discharge assembly 425 is disposed on the flow line 401 upstream of the static mixer 415. The discharge assembly 425 includes piping and a valve to control product flow between the flow line 401 and the sample receiving assembly 480. The position of the suction assembly 420 and the discharge assembly 425 on opposite sides of the static mixer 415 is exemplary and illustrative only. In some embodiments, the suction assembly 420 and the discharge assembly 425 may be on the same side of the static mixer 415. In some embodiments, the suction assembly 420 and the discharge assembly 425 may be combined into a single concentric line (FIG. 5).

The sample receiving assembly 480 includes suction piping 430 that is configured to couple with the suction assembly 420, and discharge piping 433 that is configured to couple with the discharge assembly 425. The suction piping 430 and the discharge piping 433 may include rigid piping, flexible piping, or combinations thereof. Sampling, measurement, and detection devices may tap into the suction piping 430. An automatic sampler 435 may be coupled to and receive product flow from the suction piping 430. The automatic sampler 435 may include sample tanks, tubing, and, optionally, a bite checker. An optional water detector 440 may be coupled to and sample product from the suction piping 430. A manual sampler 445 may be coupled to and receive flow from the suction piping 430. An optional densitometer/Coriolis flowmeter 450 may be coupled to and received flow from the suction piping 430. An optional viscometer 455 may be coupled to and sample product from the suction piping 430. A pump 460 may be disposed between the suction piping 430 and the discharge piping 433 to drive the product flow through the sample receiving assembly 480. In some embodiments, the pump 460 may be capable of reversing the product flow (either by reversing the motor or switching the orientation of the pump) to reverse the product flow. By reversing the pump 460, the sample receiving assembly 480, flow may be reversed without switching around the suction piping 430 and the discharge piping 433.

Figure 4B:
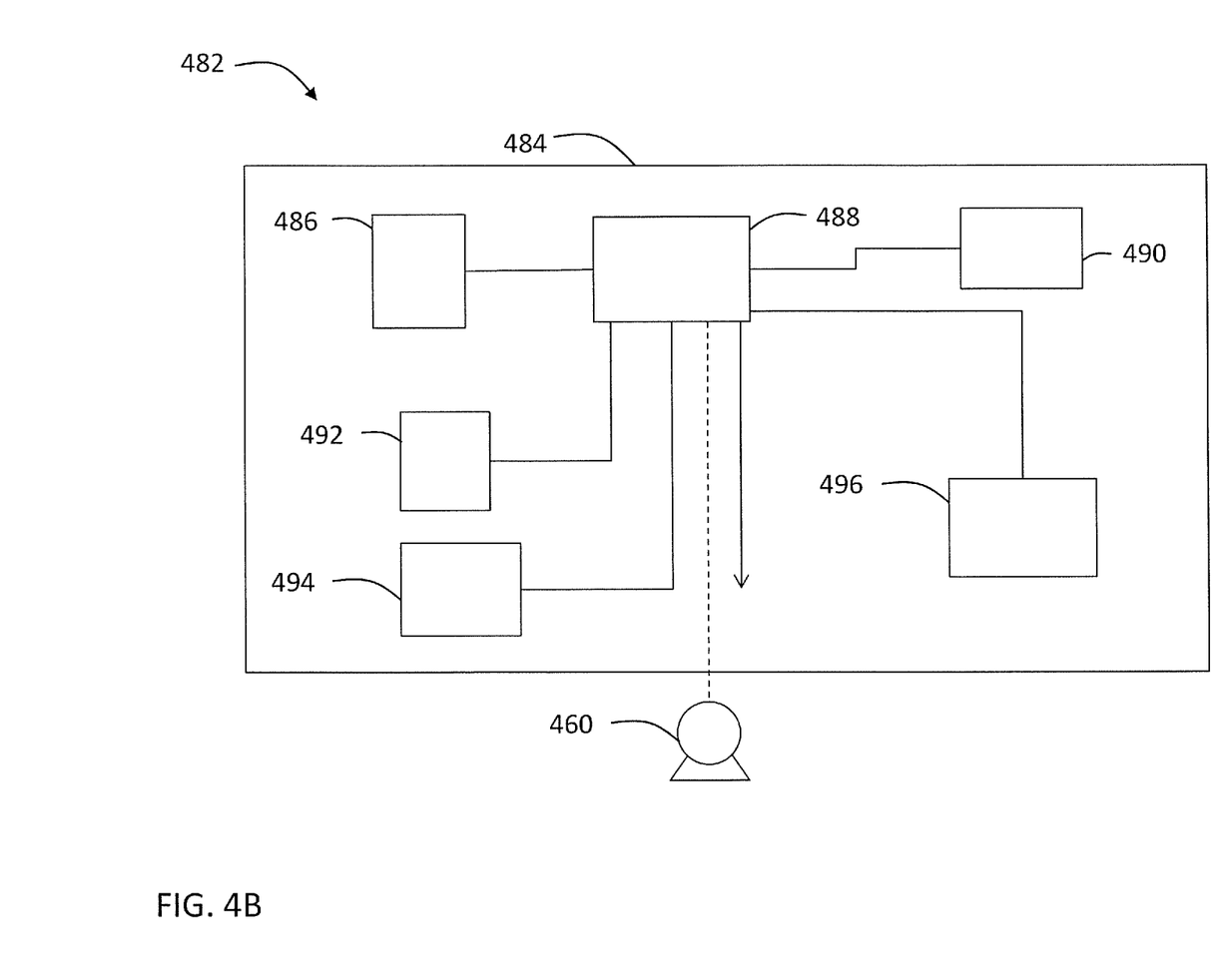
FIG. 4B shows a diagram of a monitoring and sampling panel for the product sampling system of FIG. 4A.

FIG. 4B shows an embodiment of a monitoring and sampling panel 482 for use with the assembly 400 shown in FIG. 4A. The monitoring and sampling panel 482 may include a housing 484, flowmeter electronics 486 coupled to the flow meter 405, a programmable logic controller and/or flow computer 488, and a power supply 490. The power supply 490 may be configured to supply power to the sample receiving assembly 480 and, optionally, the product sampling and mixing assembly 470 of the system 400. The monitoring and sampling panel 482 may also include optional water detector electronics 492 coupled to the optional water detector 440, optional densitometer electronics 494 coupled to the optional densitometer/Coriolis flowmeter 450, and/or optional viscometer electronics 496 coupled to the optional viscometer 455. The monitoring and sampling panel 484 may include additional measurement devices, such as a pressure transducer, a temperature transducer, and a weigh scale for sample tanks coupled to the automatic sampler 435, as would be understood by a person of ordinary skill in the art. The programmable logic controller/flow computer 488 receives power from the power supply 490 and is in electronic communication with one or more of: the flowmeter electronics 486, the optional water detector electronics 492, the optional densitometer electronics 494, and the optional viscometer electronics 496. The programmable logic controller and/or flow computer 488 may use data signals from the measurement and detection devices to computer flow rate and regulate the pump 460. Control logic in the programmable logic controller 488 may be used to set, monitor, and initiate a shutdown of the pump in response to programed safety parameters being exceeded. The control logic may also be used to control sampling timing and compute trends of the data from the input devices. The programmable logic controller and/or flow computer 488 may also transmit flow measurement and product quality data to data storage on-site or to a remote receiving station (not shown). The power supply 490 may supply power directly to devices on the product sampling and mixing assembly 470 and the sample receiving assembly 480 or may supply power indirectly to devices on the product sampling and mixing assembly 470 and the sample receiving assembly 480 by supplying power through their corresponding electronics on the monitoring and sampling panel 482.

In operation, the slip-stream hybrid product sampling system 400 may be operated using the method 300, though the coupling operation may be different. The assembly 400 may include more piping and portable devices, but allows the sampling to be performed outside of the product flow though the flow line 401, which corresponds to the tubular 14.

FIG. 5 shows a slip-stream hybrid product sampling system 500, which may be used as an alternative to system 400 or assembly 120. The system 500 includes a product sampling and mixing assembly 570 and a sampling receiving assembly 580. In operation as part of the system 100, a second product sampling and mixing assembly 570 may be used as well. The product sampling and mixing assembly 570 incorporates many of the elements of the assembly 470, and also includes a second water injection line 510 and a second spot sample port 511, both disposed on the flow line 401. By disposing the second water injection line 510 and the second spot sample port 511 on the opposite side of the static mixer 415 from the water injection line 410 and the spot sample port 411, the product sampling and mixing assembly 570 is new configured to operate bidirectionally.

The product sampling and mixing assembly 570 may also include an optional combined suction/discharge assembly 520. The combined suction/discharge assembly 520 makes the suction and discharge lines concentric and/or coaxial so that product flow from the flow line 401 may enter the suction line and then return to the flow line 401 through the annular region between the suction line and the discharge line, which reduces the risks of incorrect connection and leakage. As would be understood by a person of skill in the art, the suction and discharge may be reversed so that the discharge line is surrounded by the suction line so that the suction flow is through the annular region between the suction line and the discharge line. The combined suction/discharge assembly 520 is shown disposed on the flow line 401 downstream of the static mixer 415; however, this is illustrative and exemplary only as the combined suction/discharge assembly 520 may be installed upstream of the static mixer 415. The sample receiving assembly 580 includes a coupling 525 that can mate with the combined suction/discharge assembly and, optionally, separate the suction and discharge flows in separate lines that connect to the suction piping 430 and the discharge piping 433. In some embodiments, it is contemplated that the coupling 525 may be part of the product sampling and mixing assembly 570 such that sample receiving assembly 480 from FIG. 4A may be coupled to the product sampling and mixing assembly 570. In some embodiments, the combined suction/discharge assembly 520 and the coupler 525 are optional, and, as an alternative, the product sampling and mixing assembly 570 and the sample receiving assembly 580 may be coupled together using the suction assembly 420 and the discharge assembly 425 as shown in FIG. 4A.

Figure 6:
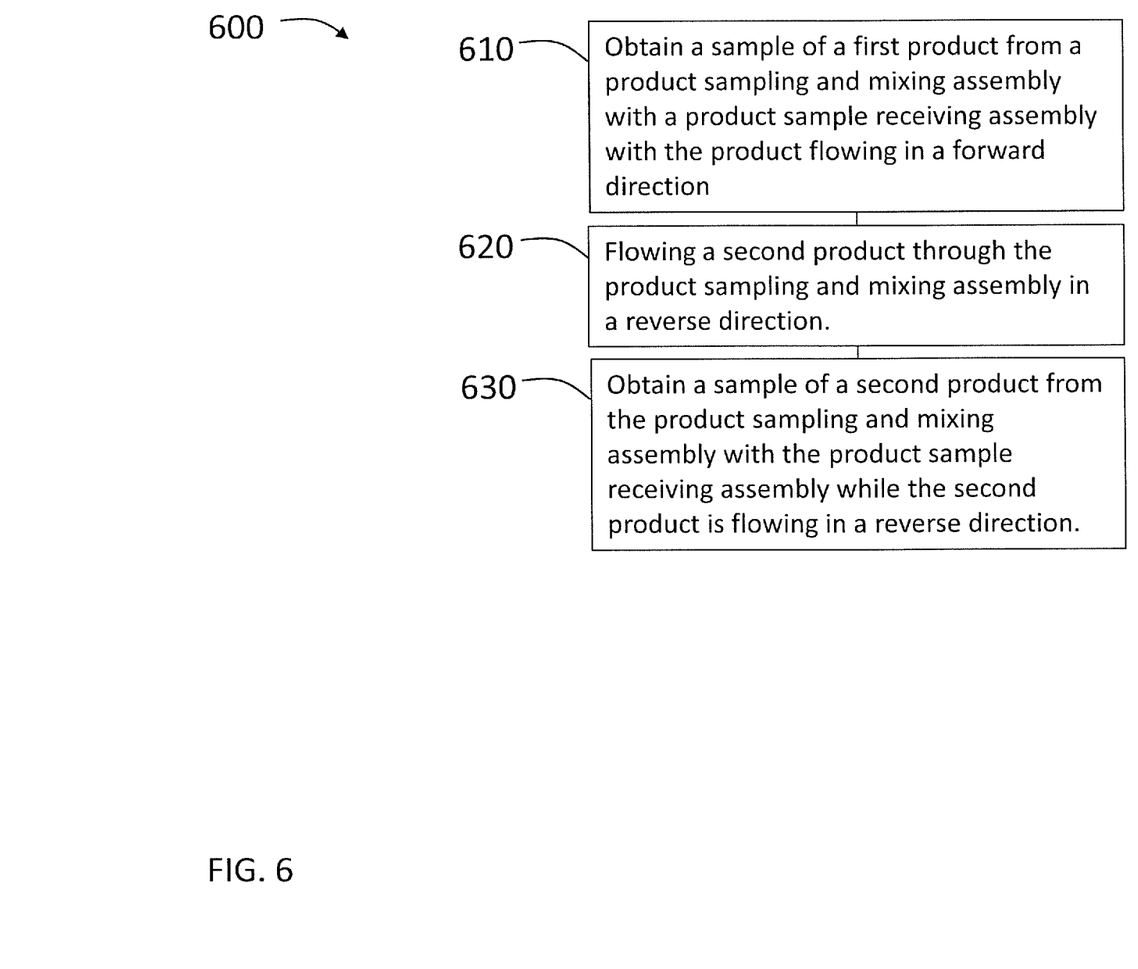
FIG. 6 shows a flow chart of an embodiment of a method for using the bidirectional product sampling and mixing assembly and portable sampling assembly with a slip-stream configuration of FIG. 5 in bidirectional mode.

FIG. 6 shows a flow chart of a method 600 for operating the system 500 in bidirectional mode. In step 610, a first sample is obtained from the product sampling and mixing assembly 570 with the sample receiving assembly 580 while a first product is flowing through the product sampling and mixing assembly 570 in a forward direction. The forward direction is from upstream to downstream in the flow line 401, which are defined by the position of the static mixer 415 on said flow line 401. In step 620, a second product is flowed through the product sampling and mixing assembly 570 in a reverse direction (e.g. the opposite of the forward direction). In step 630, a second sample is obtained from the product sampling and mixing assembly 570 with the sample receiving assembly 580 while the second product is flowing in the reverse direction. The first and second products may be the same or different materials.

While the various embodiments of the present invention disclosed herein have been made in the context of crude oil fluid sampling, it will be appreciated that the inventive concepts taught herein have application to all types of liquid products. Moreover, the application of these inventions is not limited to the oil and gas industry, but may be implemented anywhere that it is desirable that a flow stream of liquids be sampled.

All of the methods, processes, and/or apparatus disclosed and claimed herein can be made and executed without undue experimentation in light of the present disclosure. While the methods and apparatus of this invention have been described in terms of preferred embodiments, it will be apparent to those of skill in the art that variations may be applied to the methods, processes and/or apparatus and in the steps or in the sequence of steps of the methods described herein without departing from the concept and scope of the invention. More specifically, it will be apparent that certain features which are both mechanically and functionally related can be substituted for the features described herein while the same or similar results would be achieved. All such similar substitutes and modifications apparent to those skilled in the art are deemed to be within the scope and concept of the invention.

While embodiments in the present disclosure have been described in some detail, according to the preferred embodiments illustrated above, it is not meant to be limiting to modifications such as would be obvious to those skilled in the art.

The foregoing disclosure and description of the disclosure are illustrative and explanatory thereof, and various changes in the details of the illustrated apparatus and system, and the construction and the method of operation may be made without departing from the spirit of the disclosure.

What is claimed is:

1. A product sampling system comprising:
   a product sample receiving assembly suitable for liquid fluids;
   a first product sampling and mixing assembly releaseably connected to the product sample receiving assembly; and a second product sampling and mixing assembly, wherein the product sample receiving assembly is configured to connect with the second product sampling and mixing assembly when the product sample receiving assembly is detached from the first product sampling and mixing assembly; and wherein each of the first and second product sampling and mixing assemblies comprises:

a tubular;

a static mixer disposed in the tubular, wherein the static mixer defines an upstream side and a downstream side of the tubular;

a suction assembly disposed on the downstream side of the tubular;

a discharge assembly disposed on the upstream side of the tubular;

a flow meter disposed on the upstream side of the tubular; and a water injection port disposed on the upstream side of the tubular between the flow meter and the static mixer.

2. The system of claim 1, wherein the product sample receiving assembly further comprises:

suction piping configured to couple with the suction assembly;

discharge piping configured to couple with the discharge assembly; and a pump disposed between the suction piping and the discharge piping.

3. The system of claim 2, wherein the product sample receiving assembly further comprises:

a sampler in communication with the suction piping.

4. The system of claim 2, wherein the product sample receiving assembly further comprises:

a water detector in communication with the suction piping.

5. The system of claim 2, wherein the product sample receiving assembly further comprises:

a flowmeter in communication with the suction piping.

6. The system of claim 2, wherein the product sample receiving assembly further comprises:

a viscometer in communication with the suction piping.

7. The system of claim 1, wherein at least one of the first and second product sampling and mixing assemblies further comprises:

a spot sample port on the downstream side of the tubular.

8. A method of operating a product sampling system, the product sampling system comprising:

a product sample receiving assembly suitable for liquid fluids;

a first product sampling and mixing assembly releaseably connected to the product sample receiving assembly; and a second product sampling and mixing assembly, wherein the product sample receiving assembly is configured to connect with the second product sampling and mixing assembly when the product sample receiving assembly is detached from the first product sampling and mixing assembly; and wherein each of the first and second product sampling and mixing assemblies comprises:

a tubular;

a static mixer disposed in the tubular, wherein the static mixer defines an upstream side and a downstream side of the tubular;

a suction assembly disposed on the downstream side of the tubular;

a discharge assembly disposed on the upstream side of the tubular;

a flow meter disposed on the upstream side of the tubular; and a water injection port disposed on the upstream side of the tubular between the flow meter and the static mixer; and the method comprising the steps of:

obtain a sample of product from a first product sampling and mixing assembly with a product sample receiving assembly;

detach the product sample receiving assembly from the first product sampling and mixing assembly; and attach the product sample receiving assembly to a second product sampling and mixing assembly, wherein both of the first and second product sampling and mixing assemblies are configured to be releaseably attached to the product sample receiving assembly.

* * * * *